(12) United States Patent
Butler et al.

(10) Patent No.: US 9,149,419 B2
(45) Date of Patent: Oct. 6, 2015

(54) ORAL CARE PRODUCT

(75) Inventors: Michael Francis Butler, Sharnbrook (GB); Yan Deng, Shanghai (CN); Mary Heppenstall-Butler, Sharnbrook (GB); Andrew Joiner, Wirral (GB); Haiyan Li, Bordeaux (FR)

(73) Assignee: Conopco, Inc., Englewood Cliffs, NJ (US)

( * ) Notice: Subject to any disclaimer, the term of this patent is extended or adjusted under 35 U.S.C. 154(b) by 582 days.

(21) Appl. No.: 12/517,560

(22) PCT Filed: Dec. 4, 2007

(86) PCT No.: PCT/EP2007/063250
§ 371 (c)(1),
(2), (4) Date: Jan. 27, 2010

(87) PCT Pub. No.: WO2008/068247
PCT Pub. Date: Jun. 12, 2008

(65) Prior Publication Data
US 2010/0136067 A1 Jun. 3, 2010

(30) Foreign Application Priority Data

Dec. 5, 2006 (WO) ............... PCT/CN2006/003278

(51) Int. Cl.
| | |
|---|---|
| A61K 8/02 | (2006.01) |
| A61K 8/24 | (2006.01) |
| A61K 8/25 | (2006.01) |
| A61K 33/06 | (2006.01) |
| A61K 33/08 | (2006.01) |
| A61K 33/10 | (2006.01) |
| A61K 33/42 | (2006.01) |
| A61K 45/06 | (2006.01) |
| A61Q 11/00 | (2006.01) |

(52) U.S. Cl.
CPC ... *A61K 8/24* (2013.01); *A61K 8/25* (2013.01); *A61K 33/06* (2013.01); *A61K 33/08* (2013.01); *A61K 33/10* (2013.01); *A61K 33/42* (2013.01); *A61K 45/06* (2013.01); *A61Q 11/00* (2013.01)

(58) Field of Classification Search
CPC ........... A61Q 11/00; A61K 8/19; A61K 8/24; A61K 8/25; A61K 8/73; A61K 8/733; A61K 9/0056; A61K 33/00; A61K 33/06; A61K 33/08; A61K 33/10; A61K 33/42; A61K 45/063

See application file for complete search history.

(56) References Cited

U.S. PATENT DOCUMENTS

| | | | |
|---|---|---|---|
| 3,929,493 A | 12/1975 | Lee, Jr. et al. | |
| 4,038,380 A | 7/1977 | Cordon | |
| 4,080,440 A | 3/1978 | DiGiulio et al. | |
| 4,083,955 A | 4/1978 | Grabenstetter et al. | |
| 4,330,519 A | 5/1982 | Takahashi et al. | |
| 4,612,053 A | 9/1986 | Brown et al. | |
| 4,707,504 A * | 11/1987 | Walkowiak et al. | .......... 523/109 |
| 4,725,576 A | 2/1988 | Pollock et al. | |
| 5,504,958 A | 4/1996 | Herzog | |
| 5,605,675 A | 2/1997 | Usen et al. | |
| 5,726,138 A * | 3/1998 | Tsaur et al. | .................... 510/158 |
| 5,858,333 A | 1/1999 | Winston et al. | |
| 6,086,374 A | 7/2000 | Litkowski et al. | |
| 6,338,751 B1 | 1/2002 | Litkowski et al. | |
| 6,482,444 B1 | 11/2002 | Bellantone et al. | |
| 6,485,708 B1 | 11/2002 | Winston et al. | |
| 6,491,900 B2 | 12/2002 | Chow et al. | |
| 2002/0037258 A1 | 3/2002 | Dodd et al. | |
| 2002/0081555 A1 | 6/2002 | Wiesel | |
| 2002/0164472 A1 | 11/2002 | Sugimura et al. | |
| 2002/0176828 A1 | 11/2002 | Barth et al. | |
| 2002/0197214 A1 * | 12/2002 | Bublewitz et al. | ............... 424/53 |
| 2003/0099740 A1 * | 5/2003 | Colle et al. | ........................ 426/3 |
| 2003/0170185 A1 | 9/2003 | Takatsuka et al. | |
| 2003/0203206 A1 | 10/2003 | Fujiwara et al. | |
| 2003/0219388 A1 | 11/2003 | Kropf et al. | |
| 2004/0087429 A1 | 5/2004 | Ogawa et al. | |
| 2004/0191187 A1 | 9/2004 | Luo et al. | |
| 2004/0241238 A1 | 12/2004 | Sepulveda et al. | |
| 2006/0018966 A1 * | 1/2006 | Lin et al. | ........................ 424/484 |
| 2006/0088480 A1 | 4/2006 | Basic | |
| 2006/0115437 A1 | 6/2006 | Hayman et al. | |
| 2006/0134219 A1 | 6/2006 | Martens et al. | |

FOREIGN PATENT DOCUMENTS

| | | |
|---|---|---|
| AU | 595803 | 12/1990 |
| CA | 2346892 A1 | 4/2000 |
| CN | 1103750 | 3/2003 |
| CN | 1554607 | 12/2004 |
| CN | 1554607 A | 12/2004 |
| CN | 1569736 A | 1/2005 |
| CN | 1739482 A | 3/2006 |
| CN | 1785862 | 6/2006 |
| CN | 1785862 A | 6/2006 |
| EP | 0012008 A2 | 6/1980 |
| EP | 1072253 A1 | 1/2001 |
| EP | 0845976 B1 | 3/2004 |
| JP | 0531166 A | 2/1993 |

(Continued)

OTHER PUBLICATIONS

Nonami T, and S Tsutsumi. 1999. Study of diopside ceramics for biomaterials. J. Mater. Sci. Mater. Med.; 10(8): 475-479.*

(Continued)

*Primary Examiner* — Johann R Richter
*Assistant Examiner* — David Browe
(74) *Attorney, Agent, or Firm* — Greenberg Traurig, LLP

(57) ABSTRACT

An Oral care product is provided which includes a mesoporous calcium silicate biomaterial (MCSB) dispersed in a polymeric material matrix. MCSB is an insoluble composite material of calcium oxide-silica.

9 Claims, 4 Drawing Sheets

(56) References Cited

FOREIGN PATENT DOCUMENTS

| WO | 98/07558 | 2/1998 |
| --- | --- | --- |
| WO | WO9807448 | 2/1998 |
| WO | 0110392 A2 | 2/2001 |
| WO | WO0230381 A1 | 4/2002 |
| WO | WO02096391 A1 | 12/2002 |
| WO | 2004/017929 A2 | 3/2004 |
| WO | WO2004017929 A2 | 3/2004 |
| WO | WO2005063185 A1 | 7/2005 |
| WO | WO2006052743 A1 | 5/2006 |
| WO | WO2006099748 A1 | 9/2006 |
| WO | 2008/015117 A2 | 2/2008 |
| WO | WO2008015117 A2 | 2/2008 |
| WO | WO2008068247 A1 | 6/2008 |
| WO | WO2008068248 A1 | 6/2008 |

OTHER PUBLICATIONS

Butler et al. U.S. Appl. No. 12/517,562; For: Oral Care Product; International Publication No. WO 2008/068248 A1.

Berge, et al., "Pharmaceutical Salts", Journal of Pharmaceutical Sciences (1977), vol. 66 1:1-19.

Chen, et al., "Preparation of mesoporous tin oxide for electrochemical applications", Chemical Communications (1999) p. 1829-1830.

Garnier, et al., "New Amphiphilic Diblock Copolymers: Surfactant Properties and Solubilization in Their Micelles", American Chemical Society—Langmuir (2006), 22:4044-4053.

Martinez, et al., "Bioactivity of a CaO—SiO2 Binary Glasses System", American Chemical Society—Chemical Materials (2000), 12:3080-3088.

Rathod, et al., "Monodisperse Mesoporous Microparticles Prepared by Evaporation-Induced Self Assembly Within Aerosols", Materials Research Society (2003), vol. 775 p. 1.11.1-1.11.6.

Saravanapavan, et al., "Mesoporous Calcium Silicate Glasses. I. Synthesis", Journal of Non-Crystalline Solids (2003), 318:1-13.

Yan, et al., "Mesoporous Bioactive Glasses. I. Synthesis and Structural Chracterization", Journal of Non-Crystalline Solids (2005), 351:3209-3217.

ECETOC JACC No. 51, Synthetic Amorphous Silica, European Centre for Ecotoxicology and Toxicology of Chemicals (2002), p. 38, ISSN-0773-6339-51.

Berggren et al., Surfactant-templated mesostructured materials from inorganic silica, Soft matter, May 27, 2005, 1, 219-226.

Dujardin et al., Bio-inspired materials Chemistry, Advanced Materials, Jun. 5, 2002, vol. 14—No. 11, 775-787, The British Library.

Hench, Biomaterials a forecast for the future, Biomaterials 1998 vol. 19 pp. 1419., 1998, 19, 1419-1423, Elsevier Science Ltd.

Hench, Bioceramics, J Am Ceram 1998 vol. 81-7 p. 1705, 1998, 81-7, 1705-1728, The British Library.

Horejada et al., Bioactivity in ordered mesoporous materials, Solid State Science, 2004, 6, 1295-1300, Elsevier.

Kokubo, Apatite Formation on Surfaces of Ceramics, metals and polymers in Body Environment, Acta Mater, 1998, 46-7, 2519-2527, Elsevier Science Ltd., Great Britain.

Lopez et al., Growth of hydroxyapatite in a biocompatible mesoporous, Acta Biomaterialia, 2006, 2, 173-179, Elsevier Ltd.

Pereira et al., Mechansisms of Hydroxyapaptite Formation on Porous Gel-Silica Substrates, Journal of Sol-Gel Science and Technology, 1996, 7, 59-68, Kluwer Academic Publishers, The Netherlands.

Yan et al., Highly Ordered Mesoporous Bioactive glasses with Superior In Vitro Bone-Forming Bioactivities, Angew Chem Int Ed, 2004, 43, 5980-5984.

Zhao et al., Triblock Copolymer Syntheses of Mesoporous Silica with Periodic 50 to 300 Angstrom Pores, Science, Jan. 23, 1998, 279, 548-552.

DMSO Dimethyl Sulfoxide(DMSO)Solubility Data, Gaylord Chemical Company LLC, Oct. 1, 2007, Bulletin # 102b.

Butler et al. U.S. Appl. No. 12/309,789; Title: Biomaterials, Their Preparation and Use, 2009.

EP Notice of Opposition to European Patent No. EP2089039, Application No. EP07866282.2, dated Dec. 6, 2013.

European Centre for Ecotoxicology and Toxicology of Chemicals, Synthetic Amorphous Silica (CAS No. 7631-86-9), (2002), pp. 1-237, Relevant Page: p. 38, ISSN-0773-6339-51.

* cited by examiner

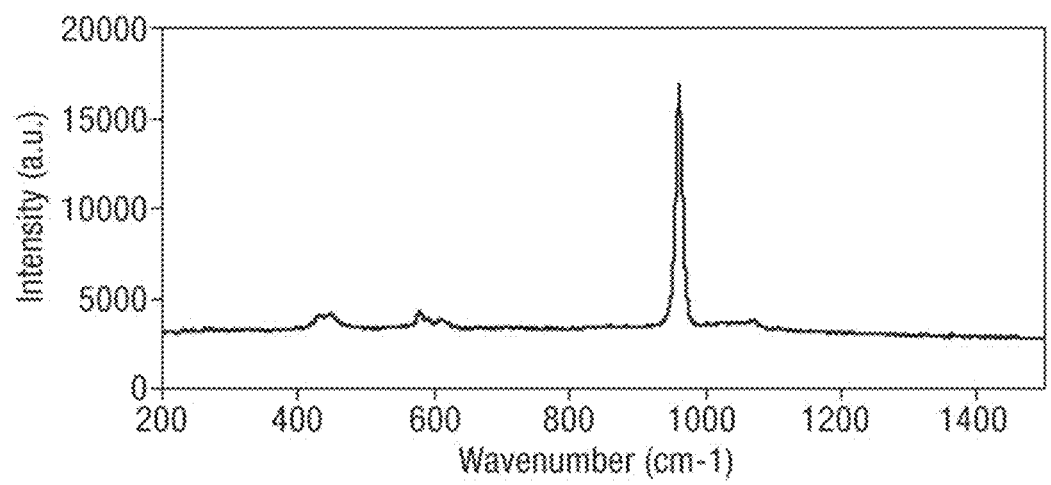
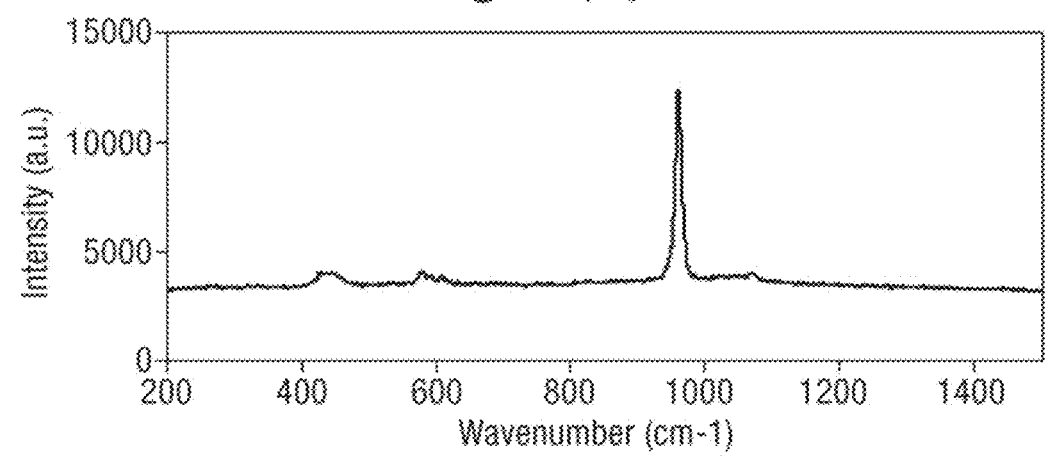

ORAL CARE PRODUCT

CROSS-REFERENCES

This application claims priority under 35 U.S.C. 119 to PCT/CN2006/003278 with filing date of Dec. 5, 2006.

The present invention relates to a polymeric material matrix comprising calcium silicate biomaterial, the preparation of such materials as well as the use of such a material to form a hydroxyapatite film on tooth surface for the remineralisation and whitening of the teeth.

A tooth is comprised of an inner dentin layer and an outer hard enamel layer that is the protective layer of the tooth.

Due to today's lifestyles with increasing consumption of acidic drinks and foods, tooth erosion is becoming more prevalent and common, which is believed to be one of the biggest threats to teeth in the 21$^{st}$ century. Enamel is the hard, protective coating of the tooth, which protects the sensitive dentin underneath. Acidic drinks and foods, such as fruit and fruit juices, can make enamel softer and wear away by acid attack. If without intervention or effective treatment, tooth erosion could further lead to tooth sensitivity with severe pain, when the surface enamel is worn off and the inner dentin tubules are exposed.

Nowadays remineralisation is usually done by adding fluoride ions according to the following reaction scheme

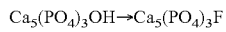

$$Ca_5(PO_4)_3OH \rightarrow Ca_5(PO_4)_3F$$

The hydroxy ion is replaced by the fluoride ion. The resulting fluoride apatite composition is harder than the hydroxy apatite composition and more resistant to the acidic attack. For that reason a majority of oral care products contain fluoride ions. However, such ion replacement through fluoride treatment cannot achieve a complete restoring of the lost minerals. It only aims to stop erosion from getting worse. So, this method is basically a preventive treatment and does not actively recover the demineralised tooth to its original chemical and mechanical states.

The enamel layer of the tooth is naturally an opaque white or slightly off-white colour; however, this enamel layer can become stained or discoloured. The enamel layer of the tooth is composed of hydroxyapatite mineral crystals that create a somewhat porous surface. It is believed that this porous nature of the enamel layer allows staining agents and discolouring substances to permeate the enamel and discolour the tooth.

Many substances can stain or reduce the whiteness of one's teeth; in particular, certain foods, tobacco products, and fluids such as tea and coffee. These staining and discolouring substances are often able to permeate the enamel layer. This problem occurs gradually over many years, but imparts a noticeable discoloration of the enamel of one's teeth.

A variety of products are currently used for teeth whitening. Such products often comprise a peroxide compound (alone or on combination with enzymes). Such products may be used in the form of strips. Such products generally have to be removed after a well defined time, the peroxide causing damage to the teeth and/or gums if left too long. A particular problem with peroxide (and toothpastes comprising abrasive cleaners) is that it can roughen the surface of the teeth.

Certain prior art treatments are known to lead to the production of hydroxyapatite on the tooth surface.

U.S. Pat. No. 5,605,675 (Enamelon, 1997) discloses a process for remineralisation of dental enamel by application of a two-phase composition; one phase containing a water-soluble calcium compound and one phase containing a water soluble inorganic phosphate and a water-soluble fluorine compound.

U.S. Pat. No. 4,083,955 (P&G, 1978) discloses a process for remineralisation of dental enamel by sequential application of two compositions, the first comprising calcium ions and second comprising phosphate ions, or vice versa.

WO 04/017929 (Septodont ou Specialites Sepodont S.A., 2004) discloses a preparation containing: an aqueous liquid part, a solid part comprising at least one silicate selected from tricalcium silicate and dicalcium silicate; calcium chloride and a water reducing agent, to be used to restore a mineralised substance, particularly in the dental field.

An object of the present invention is to provide a composition which re-mineralises the eroded teeth and which simultaneously whitens the teeth. This object may be achieved without using bleaching chemicals, thereby avoiding the disadvantages as described above.

The present invention involves delivering mesoporous calcium silicate to the surface of the teeth and ultimately converting this material into hydroxyapatite in situ by reaction with phosphate ions present in the saliva and/or added the teeth from a simultaneous or sequential applied source.

The in situ generation of hydroxyapatite results in the remineralisation of the teeth, potentially reducing the likelihood of tooth decay and improving the appearance of the teeth, in particular their whiteness. The teeth may also appear smoother and shinier as a result. Since many "whitening" treatments result in a roughening of the tooth surface, the ability to whiten and yet reduce surface roughness is a particular benefit of the present invention.

The benefits delivered by the present invention are principally targeting at the enamel; however, it is also expected that any exposed dentin may also be beneficially affected.

In a first aspect of the present invention, there is provided an oral care product comprising a mesoporous calcium silicate biomaterial dispersed in a polymeric material matrix.

In a second aspect of the present invention, there is provided a method of delivering a mesoporous calcium silicate biomaterial to the teeth, said method comprising the application of the mesoporous calcium silicate biomaterial in a polymeric material matrix.

In a third aspect of the present invention, there is provided a product according to the first aspect of the invention for use as a medicament.

In a fourth aspect of the present invention, there is provided the use of mesoporous calcium silicate biomaterial and polymeric material matrix in the manufacture of an oral care product for use to improve tooth whiteness, and/or reduce tooth decay, and/or reduce sensitivity.

In the context of this invention, a MCSB is an insoluble composite material of calcium oxide-silica: $CaO$—$SiO_2$. The material is characterised by being in a mesoporous state, i.e. it is a material having pores with diameters from of 0.4 to 50 microns. The material may be in an amorphous state or in a crystalline state.

The term "insoluble" should be understood to mean insoluble in water at temperatures in the oral cavity. Typically, "insoluble" materials have a solubility of less than 0.01 mol/L at 25° C.

The term "composite" should be understood to mean a material comprising at least two different materials. The calcium oxide-silica composite biomaterials of the present invention comprise at least calcium oxide and silica.

The term "biomaterial" should be understood to mean a material that is capable of bonding to human and/or animal tissue, including living tissue (such as bone tissue and tooth dentin) and non-living tissue (such as tooth enamel) and also including both soft and hard tissue.

The term "pore size" should be understood to mean the pore diameter. The pore size may be measured using any suitable method or means known to a person skilled in the art. For example, the pore size may be measured using BET nitrogen sorption or mercury porosimetry techniques (particularly BET nitrogen sorption techniques).

It is has been found that MCSB enables efficient calcium delivery to the teeth, at least partially overcoming problems associated with premature interaction with phosphate in the saliva of the oral cavity.

It is believed that the MCSB reacts with phosphate ions to form a calcium silicate-phosphate cement (CSPC) and that this material bonds strongly to the teeth and then gradually transforms into hydroxyapatite on the tooth surface. It is believed that the high affinity of the CSPC for the tooth surface underlies the superior remineralisation and whitening benefits obtained.

As shown in this description, mesoporous calcium silicate (MCS) delivers calcium with much greater efficiency than non-mesoporous calcium silicate and MCS fuels the growth of hydroxyapatite with much greater efficiency than non-mesoporous calcium silicate.

The MCSB is a silica-based material. In other words, the biomaterial comprises a primary structure of silica, i.e. interconnected silicon and oxygen atoms. The particular structure formed by the network of interconnected silicon and oxygen atoms may be any suitable structure and will depend on several factors, including the nature of a structure-directing agent used to prepare the composite biomaterial. For example, when the structure-directing agent is CTAB typically a hexagonal porous structure is formed and when the structure-directing agent is F127® typically a cubic porous structure is formed. Calcium atoms are covalently bonded to the oxygen atoms in the silicon-oxygen network, so as to form a coherent and continuous mix of silicon, oxygen and calcium atoms. The composite material typically has a spherical shape once formed.

Typically, the pores of the MCSB have an ordered arrangement. The ordering of the pores can, for example, be detected by small angle X-ray diffraction, for example at angles of from 1° to 8° (compared to angles of 10° to 80° used for a normal crystal). Small angle X-ray diffraction is required because the pore size is larger than the atom crystal lattice. As the skilled person would appreciate, if the pores do not have an ordered arrangement, no peaks are observed in the small angle X-ray diffraction pattern. If, however, the pores have an ordered arrangement, a sharp peak is observed in the X-ray diffraction pattern.

The MCSB has a ratio of calcium to silicon (Ca:Si) that may be from 1:10 to 3:1. The Ca:Si ratio is preferably from 1:5 to 2:1, more preferably from 1:3 to 1:1, and most preferably it is about 1:2. The MCSB may comprise mono-calcium silicate, bi-calcium silicate, or tri-calcium silicate. Higher ratios of calcium to silicate are preferred because such ratios are believed to enhance active bonding to the tooth surface and subsequent transformation into hydroxyapatite; however, lower ratios are preferred for ease of obtaining the desired pH (vide infra).

Throughout this specification, ratios of calcium to silicon (Ca:Si) should be understood to be atom ratios.

In one aspect of the invention, there is present a MCSB having an average pore size (diameter) of preferably from 0.4 to 4 nm, more preferably from 0.4 to 3.5 nm, and most preferably from 0.4 to 3 nm.

In another aspect of the invention, there is a present a MCSB having an average pore size (diameter) of preferably from 2 to 4 nm, more preferably from 2 to 3.5 nm, and most preferably from 2 to 3 nm.

In a further aspect of the invention, there is present a MCSB having an average pore size (diameter) of preferably from 1 to 2.7 nm and more preferably from 1.35 to 2.45 nm.

The pore size may be measured using any suitable method or means. For example, the pore size may be measured using BET nitrogen sorption or mercury porosimetry techniques (particularly BET nitrogen sorption techniques).

The content of the MCSB is typically from 0.05 to 25%, particularly from 0.5 to 15%, and especially from 2.5 to 10% by weight of the all the composition components of the product as to be applied to the teeth. In terms of the specific composition of which it forms a part, the MCSB is typically present at from 0.1 to 50%, particularly from 1 to 30%, and especially from 5 to 20% by weight.

Preferably, the MCSB is present in a composition that is substantially free of phosphate ions. By the term "substantially free" we mean that relative to the weight of the calcium ions, the amount of phosphate ions is less than 2.5%, particularly less than 1%, more particularly less than 0.1%, and especially less than 0.01% by weight. It is possible to prepare calcium oxide-silica containing less than 0.005% by weight of phosphate ions by using high purity starting materials, for example using calcium nitride supplied by China National Pharmaceutical Group Corporation (SINOPHARM), Beijing, which has a purity of greater than 99%.

Preferably, the MCSB is present in a composition that is substantially free of fluoride ions. By the term "substantially free" we mean that relative to the weight of the calcium in the insoluble calcium salt, the amount of fluoride ions is less than 2.5%, particularly less than 1%, more particularly less than 0.1%, and especially less than 0.01% by weight.

The MCSB is preferably present in a composition having a pH of from 7 to 11, more preferably from 8 to 10.5, and most preferably from 9 to 10. Such compositions preferably comprise an acidic buffering, such as citric acid. Such agents enable the composition to be formulated at the desired pH and are particularly desirably at higher Ca:Si ratios, for example 1:1 and greater and especially 2:1 and greater.

The following method of production can be used for obtaining a preferred MCSB. This method is further described in our co-pending application PCT/EP2007/057556.

A method for preparing a calcium oxide-silica composite biomaterial having an average pore size in the range of from 0.4 to 4 nm, comprises the steps of:
(i) combining, in solution, a calcium salt, a tetra(alkyl) silicate and a structure-directing agent in the presence of an aqueous solvent whereby hydrolysis of the tetra (alkyl)silicate occurs, leading to the formation of a sol;
(ii) isolating a solid from the sol; and
(iii) calcinating the isolated solid.

In step (i) of the above method, the tetra(alkyl)silicate is hydrolysed to form silica. It is not necessary for all of the tetra(alkyl)silicate to be hydrolysed. Typically at least 80% by weight of the tetra(alkyl)silicate is hydrolysed in step (i).

Any suitable tetra(alkyl)silicate may be used in step (i) of the above method. Suitable tetra(alkyl)silicates include tetraethyl orthosilicate [TEOS] (preferred) and tetramethyl orthosilicate. It is less preferred to use tetramethyl orthosilicate because tetramethyl orthosilicate produces methanol which potentially may disrupt the formation of the ordered structure in the sol, as well as being toxic.

Any suitable concentration of tetra(alkyl)silicate may be used in step (i) of the above method. Suitable concentrations include 0.1 to 1M, particularly 0.3 to 0.6M.

Any suitable calcium salt may be used in step (i) of the above method. Suitable calcium salts include those that are substantially soluble in an aqueous solution with a pH between 8 and 10. Suitable calcium salts include calcium nitrate, calcium fluoride and calcium chloride. In one aspect, the calcium salt is calcium nitrate.

Any suitable structure-directing agent may be used in step (i) of the above method. The structure-directing agent may be a cationic or a nonionic surfactant and should be organic in nature. When the structure-directing agent is such a surfactant, the MCSB produced typically has an average pore size in the range of from about 1.7 to 2.7 nm.

A particularly suitable cationic surfactant is cetyltrimethylammonium bromide [CTAB]. When the structure-directing agent is CTAB, the MCSB produced has an average pore size of about 2.7 nm.

A suitable nonionic surfactant is dodecylamine. When dodecylamine is used, the MCSB produced has an average pore size of about 2.4 nm.

A further suitable nonionic surfactant is Pluronic F88® (ex BASF, for example), which is a nonionic block copolymer of the formula $EO_{100}PO_{39}EO_{100}$, wherein EO represents ethylene oxide and PO represents propylene oxide. When the structure-directing agent is Pluronic F88®, the MCSB produced has an average pore size of about 3.5 nm.

A further suitable structure-directing agent is Tetronic 908® (ex BASF, for example), which is a nonionic star copolymer surfactant of the formula $(EO_{113}PO_{22})_2N(CH_2)_2N(PO_{22}EO_{113})_2$. When the structure-directing agent is Tetronic 908®, the MCSB produced has an average pore size of about 3.0 nm.

A particularly preferred MCSB for use in accordance with the present invention is prepared according to the above method using, as structure-directing agent CTAB, Pluronic F88®, Tetronic 908° or dodecylamine. Especially preferred is CTAB.

The polymeric material matrix can be a gel, a hydrogel as well as an entangled polymeric solution.

By the term "gel" we mean a colloidal system in which a porous network of interconnected nanoparticles spans the volume of a liquid medium. In general, gels are apparently solid, jelly-like materials. Both by weight and volume, gels are mostly liquid in composition and thus exhibit densities similar to liquids, however have the structural coherence of a solid.

By the term "hydrogel", we mean a mainly crosslinked polymeric material, which absorbed water and which holds water. Instead of pure water it is also possible that the hydrogel absorbed an aqueous solution additionally comprising one or more other solvent which water-miscible (such as liquid alcohols, preferably ethanol) and/or comprising water soluble compounds. Usually if a hydrogel does not only comprise water, the content of the other solvent and/or compound is not more than 10 wt %. That means that the water content is usually 90-100 wt % and the content of the additional solvent(s) and/or compound(s) is 0-10 wt %.

By the term "entangled polymeric solution", we mean a non-crosslinked or slightly crosslinked polymeric material, which does not hold water.

The polymeric matrix according to present invention usually comprises water. The water content of the polymeric material matrix can vary depending on the kind of composition which has to be provided. It is possible to prepare a polymeric material matrix with a high concentration of the calcium silicate biomaterial and therefore a lower concentration of water as well as to prepare a polymeric material matrix with a low amount of the calcium silicate biomaterial and therefore a higher concentration of water. The water content can go up to 99 wt %. Preferably the water content is between 75 and 99 wt %, more preferably between 80 and 99 wt %, based on the total weight of the polymeric material matrix (without the calcium silicate biomaterial). The content of the polymeric material in the polymeric material matrix is preferably between 1 and 25 wt %, more preferably between 1 and 20 wt %, based on the total weight of the polymeric material matrix (without the calcium silicate biomaterial).

Suitable gels can be inorganic or organic in nature, having water, or aqueous solution (hydrogels), or a non-aqueous organic solvent (organogels) as the liquid component. The hydrogel is discussed below.

A gel can be either colloidal or coarse in nature (size of the particles which form the framework) and may be rigid (elastic jellies, and thixotropic gels).

Suitable organic gels may comprise polymers as described below with respect to hydrogels.

Hydrogels may consist of polyvinyl alcohol, sodium polyacrylate, acrylate polymers and copolymers with an abundance of hydrophilic groups.

Hydrogels usually comprise a crosslinked polymer.

Preferred compounds forming hydrogels are polysaccharides, polyacrylamides, and polyacrylic acids.

The polysaccharide (macromolecular carbohydrates) can be any kind of polysaccharides, like storage polysaccharides such as starch and glycogen and structural polysaccharides such as cellulose and chitin. As used herein, the term "polysaccharides" includes natural polysaccharides, synthetic polysaccharides, polysaccharide derivatives and modified polysaccharides.

Suitable polysaccharides may be storage polysaccharides, such as starch or glycogen, or structural polysaccharides, such as cellulose or chitin.

Suitable polysaccharides may include saccharide units selected from one or more of the following: isomaltose, glucose, fructose, galactose, xylose, mannose, sorbose, arabinose, rhamnose, fucose, maltose, sucrose, lactose, maltulose, ribose, lyxose, allose, altrose, gulose, idose, talose, trehalose, nigerose, kojibiose, and lactulose.

Preferred hydrogels comprise one or more polysaccharides selected from the group consisting of: tamarind gum, guar gum, locust bean gum, Tara, Fenugreek, Aloe, Chia, Flaxseed, Psyllium seed, quince seed, xanthan, gellan, welan, rhamsan, dextran, curdlan, pullulan, scleroglucan, schizophyllan, chitin, hydroxyalkyl cellulose, arabinan, de-branched arabinan, arabinoxylan, galactan, pectic galactan, galactomannan, glucomannan, lichenan, mannan, pachyman, rhamnogalacturonan, acacia gum, agar, alginates, carrageenan, chitosan, clavan, hyaluronic acid, heparin, inulin, cellodextrins, cellulose, and cellulose derivatives.

Particularly preferred hydrogels comprise polysaccharides selected from the group consisting of: sodium alginate, hydroxypropyl alginate, gum carrageenan, gum grabic, guar gum, karaya gum, chitosan, pectin, and starch.

Other preferred hydrogel forming components are the Carbopol polymer, which are commercially available from Noveon.

The polymeric material matrix can also be formed from an entangled polymeric material. It can be any kind of non-crosslinked or only slightly crosslinked polymers. The polymers (in their non-crosslinked or slightly crosslinked state) as disclosed above are suitable as well as polysiloxane compounds as disclosed in EP 1,196,137 as well as systems as described in WO 06/071677.

The polymeric matrix material that is solid in nature, i.e. excluding any associated water or other component that is a liquid at 25° C., is typically present at from 1 to 25% by weight of the composition(s) of which it is a part.

The oral compositions of the invention may be in any form common in the art, such as gel, mousse, aerosol, gum, lozenge, powder, cream, etc. and may also be formulated into systems for use in dual-compartment type dispensers.

In the compositions described in the following paragraphs, all percentages are by weight and are by weight of the total composition, unless otherwise indicated.

In accordance with a preferred aspect of the invention, there is provided a composition comprising 5 to 99.9% of a polymeric material matrix, which comprises between 75 and 99% (preferably between 80 and 99%), based on the total weight of the polymeric material matrix, of water and between 1 and 25% (preferably between 1 and 20%), based on the total weight of the polymeric material matrix, of at least one polymeric material, and 0.1 to 95% of at least one MCSB.

For the concentration of the polymeric material matrix as well as the calcium silicate based biomaterial it must be stated that there are in principle two possible kinds of compositions:
(a) Ready to Use Compositions
    A ready to use composition, is a composition which can be used directly for the whitening and remineralisation of the teeth without diluting it. In such a composition the content of the calcium silicate based biomaterial is usually not higher than 10%. Usually the content is between 0.1 and 10%, preferably between 1 and 10%, more preferably between 1 and 8%. As consequence thereof, the polymeric material matrix content is usually at least 90%. Usually the content is between 90 and 99.9%, preferably between 90 and 99%, more preferably between 92 and 98%.
(b) Concentrated Compositions
    A concentrated composition is a composition which needs to be diluted before it can be used for putting on the teeth. In such a concentrated composition the content of the calcium silicate based biomaterial can be as high as 95% and may range from 10%.

Hence, in accordance with a further aspect of the invention, there is provided a concentrated composition comprising 5 to 90% of a polymeric material matrix, which comprises between 75 and 99% (preferably between 80 and 99%), based on the total weight of the polymeric material matrix, of water and between 1 and 25% (preferably between 1 and 20%), based on the total weight of the polymeric material matrix, of at least one polymeric material, and 10 to 95% of at least one MCSB.

The compositions according to the invention are produced usually in the way that the MCSB is added to the water and in a second step the polymeric material (gel forming material, hydrogel forming compounds or entangled polymeric material) is added.

Following application of a product according to the invention, the composition may be left on the teeth for from about 1 minute to 24 hours, although a preferred period is 30 minutes to 8 hour). The process can carried out on a daily basis.

In certain preferred embodiments, oral care products according to the invention comprise an independent source of phosphate ions, i.e. a source of phosphate ions independent of the MCSB dispersed in a polymeric material matrix. Preferably, the source is a water soluble salt, typically having a solubility of 1% by weight or greater in water at 25° C. Suitable water soluble salts include tri-sodium phosphate, di-sodium hydrogenphosphate, and sodium dihydrogenphosphate.

The MCSB dispersed in a polymeric material matrix and the source of the phosphate ions are typically kept physically separate from one another by having them in independent compositions. The delivery of these independent compositions to the teeth may be sequential or simultaneous. In certain embodiments, for example dual phase toothpastes, the compositions are preferably delivered simultaneously.

When employed, the source of phosphate ions is preferably present in a composition at a concentration of from 1 mM to 1000 mM, more preferably 5 mM to 100 mM, and most preferably 10 mM to 50 mM.

In certain embodiments, the means of delivery may involve a tape, in particular an adhesive tape, onto which the source of calcium ions and the source of phosphate ions are applied, prior to the strip being placed in contact with the teeth. Using this means of delivery, the compositions can be held in close contact with tooth surface, facilitating a high concentration of calcium salt and/or source of phosphate ions close to the tooth surface. Much less of the composition(s) is/are lost into the saliva using this delivery means.

The compositions used in accordance with the invention may comprise further ingredients which are common in the art, such as:
    antimicrobial agents, e.g. Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol);
    anti-inflammatory agents such as ibuprofen, flurbiprofen, aspirin, indomethacin etc.;
    anti-caries agents such as sodium trimetaphosphate and casein
    plaque buffers such as urea, calcium lactate, calcium glycerophosphate and strontium polyacrylates;
    vitamins such as Vitamins A, C and E;
    plant extracts;
    desensitising agents, e.g. potassium citrate, potassium chloride, potassium tartrate, potassium bicarbonate, potassium oxalate, and potassium nitrate;
    anti-calculus agents, e.g. alkali-metal pyrophosphates, hypophosphite-containing polymers, organic phosphonates and phosphocitrates etc.;
    biomolecules, e.g. bacteriocins, antibodies, enzymes, etc.;
    flavours, e.g. peppermint and spearmint oils;
    proteinaceous materials such as collagen;
    preservatives;
    opacifying agents;
    colouring agents;
    pH-adjusting agents;
    sweetening agents;
    pharmaceutically acceptable carriers, e.g. starch, sucrose, water or water/alcohol systems etc.;
    surfactants, such as anionic, nonionic, cationic and zwitterionic or amphoteric surfactants;
    particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials, usually in amounts between 3 and 60% by weight of the oral care composition.

humectants such as glycerol, sorbitol, propyleneglycol, xylitol, lactitol etc.;

binders and thickeners such as sodium carboxymethylcellulose, xanthan gum, gum arabic etc. as well as synthetic polymers such as polyacrylates and carboxyvinyl polymers such as Carbopol®;

polymeric compounds which can enhance the delivery of active ingredients such as antimicrobial agents can also be included. Examples of such polymers are copolymers of polyvinylmethylether with maleic anhydride and other similar delivery enhancing polymers, e.g. those described in DE-A-3,942,643 (Colgate);

buffers and salts to buffer the pH and ionic strength of the oral care composition; and other optional ingredients that may be included are e.g. bleaching agents such as peroxy compounds e.g. potassium peroxydiphosphate, effervescing systems such as sodium bicarbonate/citric acid systems, colour change systems, and so on.

SUMMARY OF THE FIGURES

FIG. 6a Raman spectrum of phosphoric acid etched tooth surface.

FIG. 6b Raman spectrum of phosphoric acid etched tooth surface following treatment with MCS-gel composition and phosphate containing composition for one week.

The following examples serve to illustrate the invention without limiting the invention to them. If not otherwise stated the percentages and parts are by weight.

EXAMPLES

Step I

Preparation of Gel Compositions Comprising MCS

Homogeneous suspensions of fine powder MCS (Ca:Si=1:2) in distilled water were formed in a range of concentrations from approximately 0.5% to 5%, as indicated in Table 1, using ultra-sonification. Sodium alginate gel particles were then added with vigorous stirring. After about 5 to 15 minutes, uniform white gel suspensions resulted. The pH of the gel suspensions were measured and are also indicated in Table 1.

TABLE 1

| MCS Compositions | | | | |
|---|---|---|---|---|
| | 1 | 2 | 3 | 4 |
| MSC powder (g) | 0.5 | 1.5 | 3 | 5 |
| Water (g) | 100 | 100 | 100 | 100 |
| Sodium alginate (g) | 5 | 5 | 5 | 5 |
| pH | 9.32 | 9.72 | 9.76 | 10.03 |

Further compositions were prepared as described above with the sodium alginate present at 1 g, 1.5 g, and 3 g. The viscosity of the resulting composition was found to be a function of the alginate level, being higher at the higher alginate levels.

Step II

Application of the Gel Compositions Comprising MCS

Extracted human teeth were cleaned using 75% alcohol and brushed using toothpaste to remove surface bacteria and debris. The composition designated 4 in Table 1 was uniformly painted onto the teeth at a level of 1.0 g per six teeth. The teeth were then immersed in human saliva at 37° C. After eight hours, the gel was washed off with tap water and the teeth re-immersed again in the saliva at 37° C. for the rest of day. This treatment was continued for two weeks.

The human saliva used was collected from many subjects. Its calcium concentration varied from 23 to 60 ppm and its phosphorus concentration (present as phosphate ions) varied from 124 to 154 ppm.

Figure 1A:
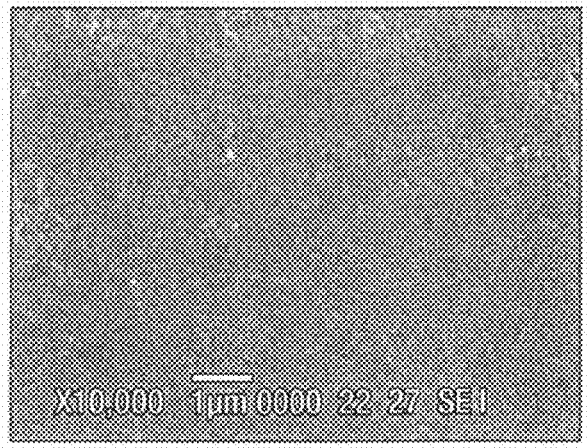
FIG. 1 Scanning electronic microscopy (SEM) image of human tooth enamel surface morphology of (a) before treatment and (b) after treatment for two weeks with MCS-gel in phosphate-containing saliva in an 8 hours/day cycling treatment.
Figure 1B:
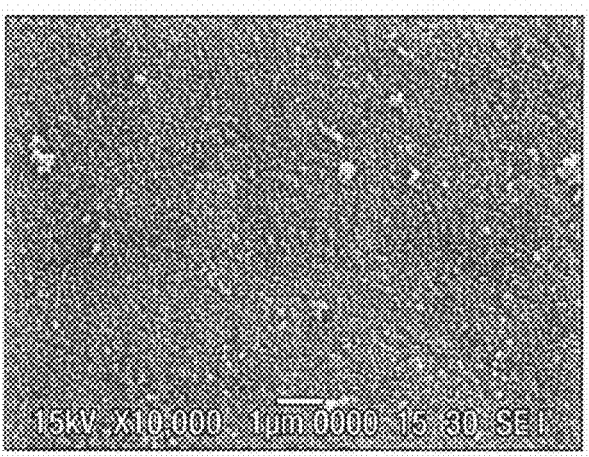

The surface morphology of the teeth was investigated using SEM before and after treatment. FIG. 1(a) represents the appearance before treatment and FIG. 1(b) represents the appearance after treatment. It can be seen that before treatment the surface is smooth and after treatment certain new crystalline structures have grown out from the original smooth surface. At a magnification of 10,000, tiny crystalline structures can be clearly seen, measuring about 100 nm.

Figure 2:
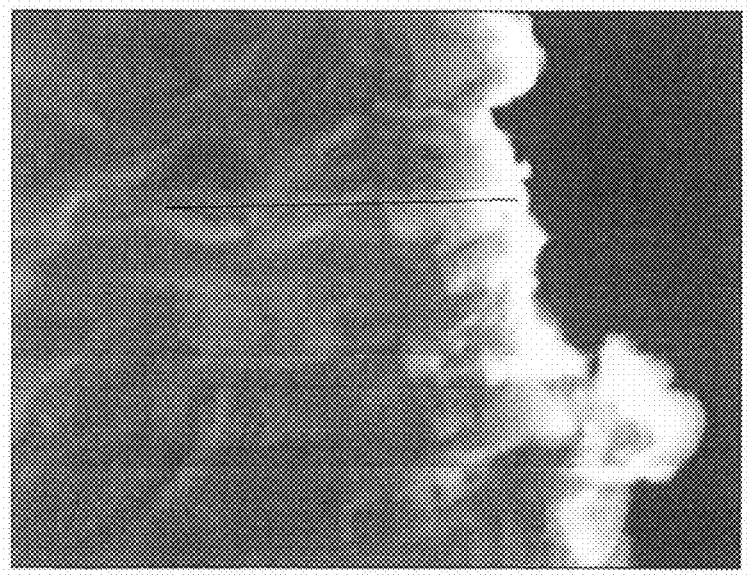
FIG. 2 SEM image of cross section view of treated tooth. A thin layer in 5 micron thickness has been formed (right bright area) on the original tooth enamel (left area).

To quantify the amount of newly formed hydroxyapatite, the before and after treatment tooth samples were sectioned and polished before being examined by SEM. The result is shown in FIG. 2. It can be clearly seen that a thin coating layer has been formed on the top of original enamel. The thickness of the layer varies from 2 to 10 microns, but seems to have a positive relation with the tooth surface roughness. Thus, it would appear that the treatment targets those teeth in most need of repair.

Figure 3:
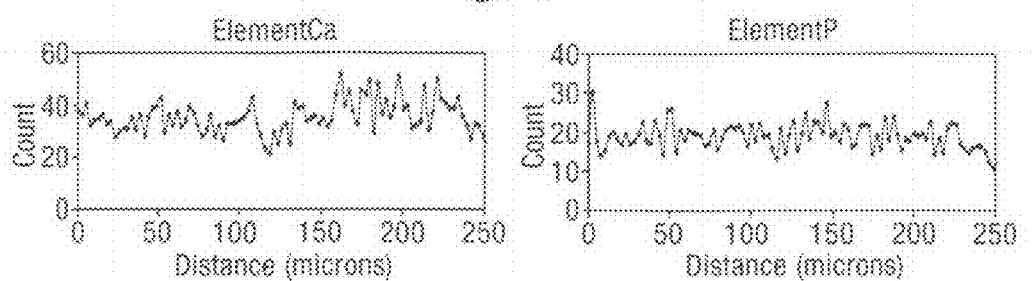
FIG. 3 Energy Dispersive X-ray (EDX) elemental analysis of Ca and P scanned (left to right) across the dark line indicated on the SEM cross-sectional image of FIG. 2. The "distances" indicated are distances in microns.
Figure 4:
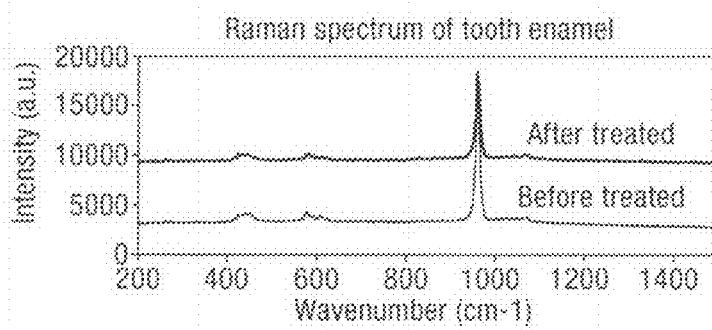
FIG. 4 Raman spectrum of tooth surface before and after MCS-gel treatment in the presence of a phosphate containing composition.

The chemical nature of the new crystalline material produced by the treatment was investigated by EDX elemental analysis (see FIG. 3) and Raman spectroscopy (see FIG. 4). FIG. 3 shows that the content of calcium and phosphorus in the newly formed hydroxyapatite is very similar to that in the original tooth enamel underneath. FIG. 4 indicates that the chemical nature of the phosphate present in newly formed hydroxyapatite is essentially the same as that of the untreated teeth, strongly suggesting that only "natural" hydroxyapatite has been added to the teeth.

Hardness Testing Using Nano-Indentation

In this experiment, the mechanical properties of the regenerated enamel layer were investigated. Mechanical robustness is of crucial importance to the long term stability of the enamel and is essential for maintenance of teeth during biting and eating food. It is desired that the enamel has a high level of mechanical hardness.

Using the same procedures as described in "Step II" (vide supra), human tooth samples were first cleaned and then treated with Composition 5 and saliva on a daily basis for two weeks. On this occasion, however, an additional step was introduced: following the eight hour immersion of painted teeth in saliva, the teeth were brushed for one minute with a chalk-containing toothpaste. They were then re-immersed in saliva as in the "Step II" procedure described above.

State of the art nano-indentation instrumentation was used to measure the hardness of the thin film of newly deposited film of hydroxyapatite on the surface of the teeth. Three treated tooth samples were measured and on each sample, nine indentations were made. As shown in Table 3, the hardness of the remineralised layer is in the range of 5.4 and 5.7 GPa. This is very close to the hardness of the original enamel surface, also shown in Table 3. Another important mechanical parameter is Young's modulus, a basic value for a material's elasticity. The higher the value, the stiffer the material is. It is desirable that the remineralisation layer is similar to the natural enamel. From the results indicated in Table 2, it is clear that the remineralised film has similar mechanical properties that that of the original enamel.

TABLE 2 mechanical properties of teeth before and after treatment

| | Hardness (GPa) | Young's modulus (GPa) |
|---|---|---|
| Before treatment (Literature values) | 5.0-6.0 | 95-120 |
| After forming new enamel layer | 5.4-5.7 | 111-121 |

Regeneration of Damaged Teeth

Figure 5A:
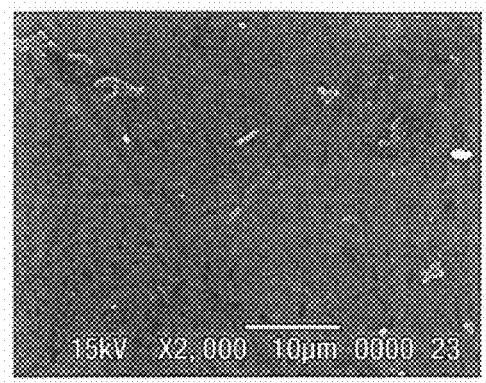
FIG. 5a SEM image of a tooth surface prior to "etching" with phosphoric acid.
Figure 5B:
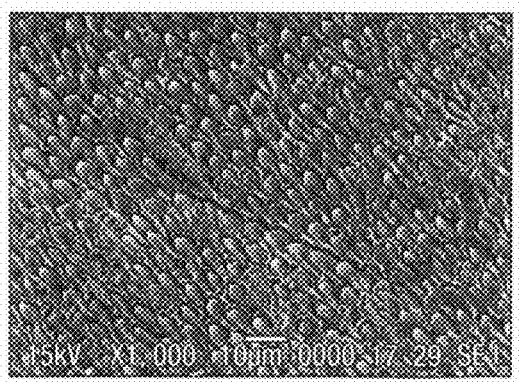
FIG. 5b SEM image of a tooth surface after etching with phosphoric acid.

To mimic the demineralization of teeth by many types of acidic fruit juice, human teeth were etched using 37 wt % phosphoric acid for one minute. Images of the original teeth and the phosphoric acid etched teeth were taken by SEM. FIG. 5a represents a tooth surface before etching and FIG. 5b represents a tooth surface after etching. By treatment with Composition 5 (described below) in the manner described above, it was found possible to cure the etching caused by the phosphoric acid within one week.

Composition 5: MCS powder (0.5 g) added to water (10 g) and dispersed as described above, then sodium alginate (0.3 g) added with vigorous stirring. A uniform gel was formed after about ten minutes stirring.

The treated samples were found to have grown a significant thickness of a new layer. The newly formed layer was characterized by Raman spectroscopy. FIG. 6a is the Raman spectrum of a tooth surface before treatment and FIG. 6b is the Raman spectrum of a tooth surface after treatment. Table 3 indicates the position of the major peaks before and after treatment. There is a peak at 961.42 cm$^{-1}$ which corresponds to the major phosphate band. The after treatment sample gave an essentially identical Raman spectrum to the before treatment sample, including the location of the phosphate band at 961.42 cm$^{-1}$. This implies that the added material is identical to that originally present and is a somewhat surprising result.

TABLE 3

Raman peaks positions of human tooth enamel before and after treatment

| Band | Position before treatment | Position after treatment |
|---|---|---|
| $v_1\ PO_4^{3-}$ | 961 | 961 |
| $v_2\ PO_4^{3-}$ | 445 | 444 |
| $v_3\ PO_4^{3-}$ | 1072 | 1069 |
| $v_4\ PO_4^{3-}$ | 579 | 579 |

The Raman bands $v_1$, $v_2$, $v_3$, and $v_4$ are characteristic of the crystallinity/perfection of the apatite crystal lattice.

Example 6

Dual Phase Gel Product

A product was prepared comprising two gel compositions: Gel I and Gel II. Details are given in Table 4. An MSC powder as described above under "step I" was incorporated into Gel I by the method disclosed under "step I". Gel II was prepared by adding sodium alginate to a solution of phosphate buffer and sodium fluoride.

TABLE 4 dual phase gel product

| | MCS Powders (wt %) | Alginate Powders (wt %) | Phosphate (mM) | Fluoride (mM) |
|---|---|---|---|---|
| Gel I | 5 | 3 | 0 | 0 |
| Gel II | 0 | 3 | 25 | 25 |

The product was applied by mixing equal weights of Gel I and Gel II and painting the mixture (total weight 2 g) onto six teeth using a cotton bud. The treated teeth were immersed in human saliva (15 ml) for one hour, at 37° C., with gentle agitation. After this time, the teeth were rinsed and cleaned using a cotton bud to remove any remaining gel. They were then placed into fresh saliva for a further two hours. This process was performed twice a day for two weeks, giving a total of 28 treatments.

In a further experiment, Example 6 as described above (i.e. a 1:1 by weight mixture of Gel I and Gel II) was applied to an adhesive plastic tape. Then the tape was then wrapped around each tooth and the wrapped teeth immersed in saliva for eight hours. The dosage applied was 2 g of the mixture of Gel I and Gel II per 6 teeth. After this time, the teeth were rinsed with water and then put into fresh saliva. This procedure was repeated for two weeks, including a tooth brushing each day to simulate real life usage.

The effects of the above treatments with Example 6, with respect to tooth whitening, were investigated together with a "control" treatment involving tooth brushing (once a day) and treatment with saliva only.

The whitening effect was measured using a Minolta Chromameter CR-321 (3 mm aperture, 45/0) to quantitatively measure the L* and b* value of each tooth before and after treatment. L* represents the overall light intensity that is reflected from the tested surface and b* represents the light contribution from the yellow-blue. Tooth whitening is indicated by an increase in reflected light intensity (L*) and a decrease in "yellowness" (b*). The results are shown in Table 5. Average colour changes after two weeks treatment are expressed as ΔL* and Δb*. Good whitening effects were observed with both treatments according to the invention.

TABLE 5

Whitening effect following treatment with Example 6

| | Application | ΔL* | ΔL* |
|---|---|---|---|
| Treatments | Painting on | 1.88 | −1.08 |
| | Strip | 4.99 | −2.24 |
| Control | Saliva only | 0.57 | −0.91 |

Examples 7-9

Dual Phase Toothpaste Products

TABLE 6

Composition details

| | First Composition | | | | Second |
|---|---|---|---|---|---|
| Component | 7 | 8 | 9 | A | Composition |
| Calcium silicate | 30 | 20 | 10 | — | — |
| Fine ground natural chalk | 10 | 20 | 30 | 40 | — |
| NaH$_2$PO$_4$ | — | — | — | — | 6.4 |
| Na$_3$PO$_4$ | — | — | — | — | 7.6 |
| Sorbitol (70% aqu.) | 20 | 20 | 20 | 20 | 64 |
| PEG 1500 | — | — | — | — | 2 |
| Abrasive silica | — | — | — | — | 9 |
| Thickening silica | — | — | — | — | 4.8 |
| Sodium lauryl sulphate | 13.5 | 13.5 | 13.5 | 13.5 | — |
| Sodium carboxymethylcellulose | 0.2 | 0.2 | 0.2 | 0.2 | 0.5 |
| Flavour | 1 | 1 | 1 | 1 | 1 |
| Saccharine | 0.3 | 0.3 | 0.3 | 0.3 | 0.3 |
| Water and minors* | 25 | 25 | 25 | 25 | 4.4 |

*0.25% potassium nitrate, 0.05% formaldehyde, and 0.15% triclosan in each "First Composition".

With reference to Table 6:

Example 7: 1:1 by weight mixture of First Composition 7 and the Second Composition;

Example 8: 1:1 by weight mixture of First Composition 8 and the Second Composition;

Example 9: 1:1 by weight mixture of First Composition 9 and the Second Composition;

Example A: 1:1 by weight mixture of First Composition A and the Second Composition.

These Examples were used to treat polished tooth enamel blocks. The treatment involved brushing with a slurry of the dual phase toothpaste in water (1 part toothpaste to 2 parts water) for 3 minutes, followed by incubation of the blocks in saliva for 2 hours at 37° C. This procedure was performed twice a day over a four week period. A conventional "whitening" toothpaste was used as a control, as was water.

The colour of the tooth enamel blocks was monitored using a Chromameter, as described above. The final results are indicated in Table 7, ΔL* and ΔW* representing the changes in "lightness" and "whiteness" between before and after treatment. "W" is a "whiteness measure" calculated as:

$$W = 100 - \sqrt{\{(100-L^*)^2 + a^{*2} + b^{*2}\}}$$

TABLE 7 whitening results following use of dual phase toothpaste products

| Example used | ΔL* | ΔW* |
|---|---|---|
| 7 | 2.32 | 1.91 |
| A | 1.21 | 1.09 |
| Toothpaste control | 0.73 | 0.36 |
| Water control | 0.56 | 0.21 |

These results indicate that Example 7 gives superior "lightening" and "whitening" in comparison with the controls.

The L* value on use of Example 7 was found to increase over time. This result is illustrated by the Figures in Table 8.

TABLE 8

Effect of duration of treatment

| | Treatment (weeks) | | | | |
|---|---|---|---|---|---|
| | 0 | 1 | 2 | 3 | 4 |
| L* | 63.52 | 64.82 | 65.37 | 65.85 | 65.84 |

The effect of the treatments on the hardness of the polished tooth enamel blocks was also investigated. This was done by measuring Knoop hardness using a HM-122 hardness testing machine (from Mitutoyo, Japan). 10 samples were measured for each treatment and 5 indentations made for each sample. The results shown in Table 9 illustrate that Examples 8 and 9 led to a significant increase ($p<0.05$) in enamel hardness.

TABLE 9 hardness results following use of dual phase toothpaste products

| | Hardness (GPa) | |
|---|---|---|
| Example used | Before | After |
| 8 | 266 | 318 |
| 9 | 276 | 333 |
| A | 281 | 271 |
| Toothpaste control | 274 | 287 |
| Water control | 296 | 283 |

The effect of the treatments on the roughness of the polished tooth enamel blocks was also investigated. This was done using a surface profilometer (SV2000 from Mitutoyo, Japan). 10 samples were measured for each treatment. The results shown in Table 10 illustrate that Examples 8 and 9 led to a significant decrease in enamel roughness, i.e., a significant increase in smoothness and shine.

TABLE 10 effect of treatments on enamel roughness

| Example used | Roughness change (%) |
|---|---|
| 8 | −10.9 |
| 9 | −10.2 |
| A | +5.2 |
| Toothpaste control | +20 |
| Water control | −2.2 |

In an independent study, the effect of the treatments upon the whiteness of whole teeth was examined. The experimental procedure was essentially the same as that described with respect to the polished tooth enamel blocks (described above), the only difference being the use of whole teeth. The results indicated in Table 11 illustrate the superior efficacy of Example 7 in comparison with a conventional whitening toothpaste.

TABLE 11 whitening results on whole teeth

| Example used | ΔL* | Δb* | ΔW* |
|---|---|---|---|
| 7 | 1.76 | −0.77 | 1.88 |
| Toothpaste control | 0.20 | −0.28 | 0.26 |

Example 10

Dual Phase Toothpaste Product

The two compositions detailed in Table 12 are intended for use in a 1:1 by weight ratio. These compositions are suitable for extrusion as independent compositions/phases from within the same compartment of the same tube, for example with the first composition forming a core and the second composition forming a surrounding sheath. The amount of water in the compositions of this Example is particularly low.

TABLE 12 dual phase toothpaste for contact extrusion

| Component | First Composition | Second Composition |
|---|---|---|
| Calcium silicate | 20 | — |
| Na$_2$HPO$_4$ | — | 10 |
| Sorbitol (70% aqu.) | 48 | 61 |
| PEG 1500 | 2 | 2 |
| Abrasive silica | 9 | 9 |
| Thickening silica | 8.5 | 7.5 |
| Sodium lauryl sulphate | 6.6 | 6.6 |
| Sodium carboxymethylcellulose | 0.6 | 0.6 |
| Flavour | 1.3 | 1.3 |
| Saccharine | 0.2 | 0.2 |
| Water and minors* | 3.8 | 1.8 |

*2 ppm blue pigment in the "First Composition".

Examples 11-13

Products with Insoluble Whitening Particles

The gel compositions shown in Table 13 were prepared as previously described with added insoluble whitening particles as indicated. These compositions were used treat hydroxyapatite discs (n=6-8) for 30 minutes per day over a 4 week period. Following the 30 minute treatment, on each day, the discs were treated with a source of phosphate ions (simulated oral fluid). The colour of the hydroxyapatite discs was monitored using a Chromameter, as described above. The final results are indicated at the bottom of Table 13.

TABLE 13

| | Example | | |
|---|---|---|---|
| Component | 11 | 12 | 13 |
| Calcium silicate | 10 | 10 | 10 |
| Sodium alginate | 3 | 3 | 3 |
| Titanium dioxide | 2.5 | 1 | — |
| Zinc oxide | — | — | 1 |
| Water | To 100 | To 100 | To 100 |
| ΔL* | 1.51 | 1.06 | 2.59 |
| Δb* | −7.53 | −2.12 | −0.79 |

These results illustrate the excellent whitening benefits that may be obtained by use of the present invention.

Example 14

Dual Phase Toothpaste Product

The two compositions ("First" and "Second") detailed in Table 14 are intended for use in a 1:1 by weight ratio.

TABLE 14

| Component | First Composition | Second Composition |
|---|---|---|
| Calcium silicate | 20 | — |
| NaH$_2$PO$_4$ | — | 10 |
| Sorbitol (70% aqu.) | 60 | 60 |
| PEG 1500 | 2 | 2 |
| Abrasive silica | 2 | 8 |
| Thickening silica | 8 | 6 |
| Sodium lauryl sulphate | 3 | 3 |
| Sodium carboxymethylcellulose | 0.4 | 0.8 |
| Flavour | 1 | — |
| Saccharine | 0.1 | 0.1 |
| Titanium dioxide | — | 5 |
| Water | 3.5 | 5.1 |

Example 15

Calcium Ion Release

Mesoporous calcium silicate (0.04 g) was dispersed in water (40 ml) using ultrasound for 5 minutes. A dispersion of non-mesoporous calcium silicate (non-MCS) of the same concentration was also prepared. Both the MCS and non-MCS had the same Ca:Si ratio (1:1).

Samples of the dispersions described above were diluted 10 times with water and the calcium concentrations measured using atomic absorption after 5 minutes and after 20 hours. The results are shown in Table 15. It is clear that the MCS releases significantly more calcium ions that the non-MCS.

TABLE 15

| | Ca concentration (ppm) | |
|---|---|---|
| Time | 5 min. | 20 hour |
| MCS (Ca:Si = 1:1) | 11.1 | 13.0 |
| Non-MSC (Ca:Si = 1:1) | 4.7 | 2.4 |

Example 16

Hydroxyapatite Growth

Figure 7:
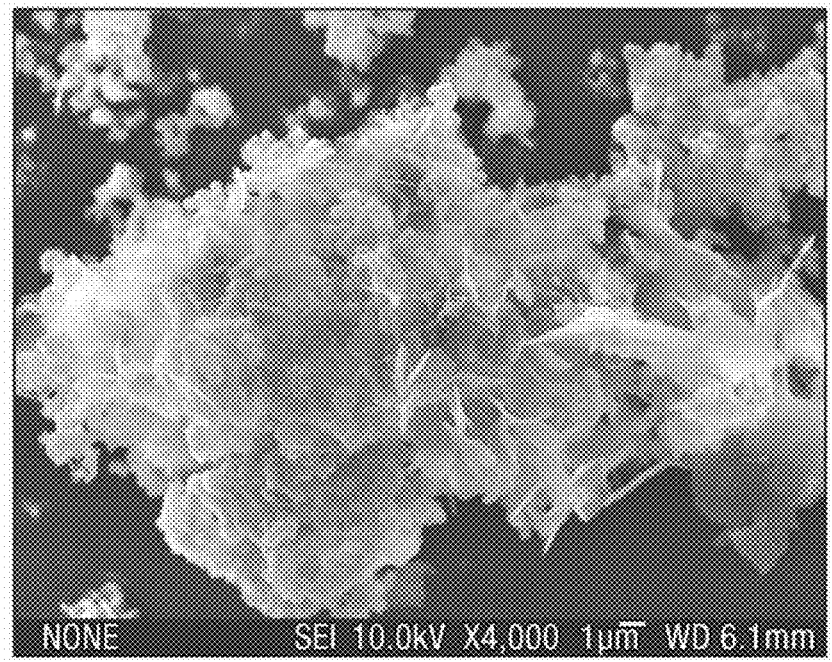
FIG. 7 SEM image of MCS following incubation with phosphate buffered saline (PBS).
Figure 8:
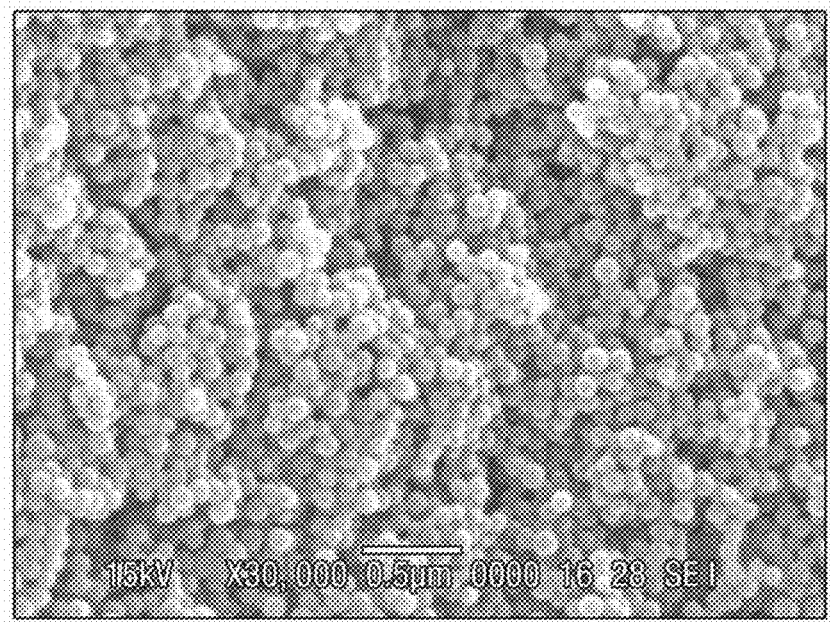
FIG. 8 SEM image of non-MCS following incubation with PBS.

In a further experiment, MSC and non-MSC were independently incubated in phosphate buffered saline (25 mM) for 24 hours at 37° C. FIG. 7 is an SEM showing extensive hydroxyapatite growth on the MSC sample. FIG. 8 is an SEM showing no significant growth of hydroxyapatite on the non-MCS sample.

We claim:

1. An oral care product comprising:
    a mesoporous calcium silicate biomaterial having a Ca:Si ratio of from 1:1 to 1:2 dispersed in a polymeric material matrix;
    wherein the polymeric material matrix comprises:
    i) water, being between 75 wt % and 99 wt % of the polymeric material matrix, and
    ii) at least one polymeric material, being between 1 wt % and 25 wt % of the polymeric material matrix;
    wherein the mesoporous calcium silicate biomaterial has an average pore size (diameter) of from 0.4 to 4 nm;
    wherein the oral care product does not include a bleaching chemical;
    wherein a weight percent of the polymeric material matrix is at least 90% of a total weight of the oral care product.

2. The oral care product according to claim 1, wherein the mesoporous calcium silicate biomaterial has a Ca:Si ratio of 1:2.

3. The oral care product according to claim 1, comprising an entangled polymer polymeric material matrix.

4. An oral care product comprising a mesoporous calcium silicate biomaterial dispersed in an alginate matrix;
    wherein the alginate matrix comprises:
    i) water, being between 75 wt % and 99 wt % of the alginate matrix, and
    ii) at least one alginate, being between 1 wt % and 25 wt % of the alginate matrix;
    wherein the mesoporous calcium silicate biomaterial has:
    an average pore size (diameter) of from 0.4 to 4 nm and a Ca:Si ratio of from 1:1 to 1:2
    wherein the oral care product does not include a bleaching chemical; and
    wherein a weight percent of the mesoporous calcium silicate biomaterial is 0.05% to 25% of a total weight of the oral care product.

5. The oral care product according to claim 4, wherein the mesoporous calcium silicate biomaterial has a Ca:Si ratio of 1:2.

6. The oral care product according to claim 1, wherein an amount of phosphate ions is less than 2.5% of the total weight of the oral care product.

7. The oral care product according to claim 1, wherein an amount of fluoride ions is less than 2.5% of the total weight of the oral care product.

8. The oral care product according to claim 4, wherein an amount of phosphate ions is less than 2.5% of the total weight of the oral care product.

9. The oral care product according to claim 4, wherein an amount of fluoride ions is less than 2.5% of the total weight of the oral care product.

* * * * *